United States Patent [19]

Estep

[11] Patent Number: 4,861,867
[45] Date of Patent: Aug. 29, 1989

[54] PURIFIED HEMOGLOBIN SOLUTIONS AND METHOD FOR MAKING SAME

[75] Inventor: Timothy N. Estep, Lindenhust, Ill.

[73] Assignee: Baxter International, Inc., Deerfield, Ill.

[21] Appl. No.: 280,111

[22] Filed: Jan. 23, 1989

Related U.S. Application Data

[60] Division of Ser. No. 151,842, Feb. 3, 1988, Pat. No. 4,831,012, which is a continuation-in-part of Ser. No. 747,477, Jun. 21, 1985, abandoned, which is a continuation-in-part of Ser. No. 592,633, Mar. 23, 1984, abandoned.

[51] Int. Cl.⁴ .............................................. C07K 15/22
[52] U.S. Cl. .................................................... 530/385
[58] Field of Search ............................. 514/6; 530/385

[56] References Cited

U.S. PATENT DOCUMENTS 4,061,736 12/1977 Morris et al. ............................ 514/6
4,439,357 3/1984 Bonhard et al. ..................... 530/385
4,456,590 6/1984 Rubinstein .......................... 424/101

Primary Examiner—Sam Rosen
Attorney, Agent, or Firm—Paul C. Flattery; Susan Bennett Fentress; Sarah E. Bates

[57] ABSTRACT

Hemoglobin solutions are purified by heating in the presence of a reducing agent or other deoxygenating conditions such that nonhemoglobin proteins are selectively precipitated and/or virus is inactivated while minimizing hemoglobin loss.

7 Claims, 2 Drawing Sheets

PURIFIED HEMOGLOBIN SOLUTIONS AND METHOD FOR MAKING SAME

CROSS REFERENCE TO RELATED APPLICATION

This is a divisional of U.S. patent application Ser. No. 151,842, filed Feb. 3, 1988 now U.S. Pat. No. 4,831,012 which is a continuation-in-part of U.S. Pat. Serial No. 747,477, filed June 21, 1985, now abandoned, which is a continuation-in-part of U.S. patent application 592,633, filed Mar. 23, 1984, now abandoned.

TECHNICAL FIELD

This invention relates to a method for purifying hemoglobin solutions. In particular it relates to a method for inactivating viruses and selectively removing non-hemoglobin proteins from hemoglobin solutions while only minimally inactivating the biological activity of the desired hemoglobin product.

In the current practice of medicine whole blood or red blood cell containing suspensions are the only oxygen carrying fluids which may be infused into patients or trauma victims. Due to the necessity for matching donor and recipient blood types the infusion of red blood cells in any form is restricted to settings in which blood typing and cross-matching may be performed. The typing and cross-matching process may take as long as 45 minutes. As a result of this requirement trauma victims suffering substantial blood loss must now be infused with non-oxygen transporting salt or colloid solutions until such time as properly typed and cross-matched blood is available. Many trauma victims are therefore subjected to periods of oxygen deprivation which may be highly detrimental or even fatal. Even in a hospital setting patients suffering acute blood loss may not receive blood in a timely fashion due to a shortage of the appropriate blood type.

Another problem associated with the infusion of blood or products derived from blood is the risk of transmission of viral contamination. Various prospective studies have shown that the incidence of posttransfusion hepatitis in recipients of hepatitis B surface antigen negative blood collected from volunteer donors ranges from 4 to 14 percent (Blum and Vyas, Haematologia, (1982), 15:153–173). There is also the risk of transmission of the virus causing Acquired Immunodeficiency Syndrome (variously called HTLV-III, LAV or HIV), cytomegalovirus, Epstein-Barr virus or HTLV-I, the putative causative agent for adult T cell lymphoma leukemia. Products derived from animal blood are also at risk since such blood may contain a number of pathogenic agents including the viruses causing rabies, encephalitis, foot-and-mouth disease, etc.

As a result of these considerations a number of researchers have investigated the possibility of using oxygen carrying resuscitation fluids based on cell-free hemoglobin solutions. The basic premise of this work is that by the removal of the oxygen-carrying hemoglobin from the red blood cell and its subsequent purification, one may eliminate the blood type specific antigens and, hopefully, the bacterial and viral contamination. While the lysis of red blood cells to release hemoglobin and the subsequent removal of the residual cell membranes (the stroma) have indeed been shown to result in the removal of type specific antigens, there is little data available on the amount of residual virus present in the various preparations which have been described in the literature. Experience with plasma proteins such as albumin suggests that viral contamination is a problem even with blood derived proteins which have been subjected to the elaborate fractionation schemes which are used to prepare these products commercially. For example, albumin prepared by commercial fractionation procedures from pooled plasma samples has a significant probability of contamination with hepatitis virus if the albumin solutions are not heat treated (Gellis et al., J. Clin. Invest. (1948), 27:239–244;). One would expect a similar situation to hold for hemoglobin solutions. It is therefore a primary objective of the invention to inactivate viruses which may be present in hemoglobin solutions.

In U.S. Pat. Nos. 3,864,478 and 4,439,357 Bonhard and coworkers claim the production of hepatitis-safe hemoglobin solutions, evidently by virtue of the fact that the red cell starting material was washed and then exposed to $\beta$-propiolactone. No data were cited, however, to indicate whether this procedure does in fact remove or inactivate viruses in hemoglobin solutions. While cell washing may reduce the number of viruses present in solution, it does not remove viruses which may be adherent to or incorporated within the cells. Moreover, while $\beta$-propiolactone (BPL) can induce some viral inactivation, Barker and Murray (J. Am. Med. Assoc., (1971), 216:1970–1976) noted that hepatitis infected plasma which was treated with BPL alone was still able to transmit the disease to human recipients. Virus inactivation with BPL often exhibits a "tailing-off" phenomenon wherein a portion of the original virus population is much more resistant to inactivation by the agent employed than is the bulk of the viruses (Hartman, J. and LaGrippo, G.A. Hepatitis Frontiers, (1957) Little, Brown and Co., Burton, Chapt. 33). Moreover, BPL is a known carcinogen (Sax, N.J., Cancer Causing Chemicals (1981), Van Nostrand Reinhold Co., New York, p. 404). In the U.S. Pat. No. 4,526,715 Kothe and Eichentopf discuss the preparation of a hepatitis-free hemoglobin solution by a method employing washing and filtration. While these authors demonstrated that washing can reduce the concentration of viruses in solution, the method suggested would to remove white blood cells. Any virus incorporated into white cells, such as HTLV-III, would not be eliminated by this processing step. Such viruses would, however, be released into solution during cell lysis. Viruses readily pass through microporous filters, and ultrafilters are known to contain pinholes which allow the passage of particles greater in size than the nominal molecular weight cut-off of the membrane. The ability of the described procedure to quantitatively remove viruses associated with white blood cells is therefore questionable. Until now, a procedure which demonstrably reduces product-related virus titers by a factor of $10^6$ or more in hemoglobin solutions, and which can reliably inactivate retroviruses which may be incorporated into the blood formed elements, has not been discovered.

On the other hand, various literature and patent sources disclose methods for inactivating viruses in blood plasma protein fractions. An effective method employs dry heat inactivation, i.e., the lyophilized protein which is suspected to bear viral contamination is simply heated in the dry state at temperatures above about 50 degrees C. until the desired viral inactivation is achieved. A representative method of this sort is disclosed in PCT publication WO 82/03871.

Another technique also employs heat, but the protein fraction is heated while in aqueous solution rather than dry. Stabilizers are included in the solutions in order to preserve the biological activity of the desired protein. For example, see U.S. Pat. Nos. 4,297,344; 4,317,086; and European patent applications 53,338 and 52,827. The stabilizers that have been used for this purpose are glycine, alpha- or beta-alanine, hydroxyproline, glutamine, alpha-, beta- or gamma-aminobutyric acid, monosaccharides, oligosaccharides, sugar alcohols, organic carboxylic acids, neutral amino acids, chelating agents and calcium ions.

These methods are both founded on the discovery that heat will inactivate viruses at a greater rate than the proteins, provided that an agent or stabilizer is present or conditions are identified which stabilize the desired protein but which do not at the same time similarly stabilize the viral contaminants.

Unfortunately, proteins are known to exhibit widely varying susceptibility to denaturation during heating due to differences in their chemical and physical structure. The biologically active form of a protein is maintained by complex interactions between its constituent amino acids. These interactions include hydrogen bonding, salt linkages between charged groups, dipole-dipole interactions, hydrophobic effects and dispersion forces. Although the factors governing protein stability in general, and hemoglobin stability in particular, have been studied for many decades, the thermal stability of a protein cannot be predicted even when the amino acid sequence is known. Bull and Breise noted a 35 degree C. spread in the denaturation temperature of twenty proteins which they studied with no correlation being evident between this temperature and protein structural features (Arch. Biochem. Biophys. (1972) 156:604-612).

Protein stability also varies as a function of the composition of the medium in which the protein is placed, being sensitive to pH, salt concentration, the present of detergents or organic solvents, and the presence or absence of ligands which may bind to the protein. For example, some proteins are easily denatured by acid pH while others are actually stabilized under these conditions (Tanford, *Physical Chemistry of Macromolecules* (1961) John Wiley and Sons, New York, p. 625; White et al., *Principals of Biochemistry* (1978) McGraw-Hil, New York, p. 164). The stabilization of proteins by ligand binding is a frequent (but not universal) occurrence, and has been used to preserve proteins during purification. This strategy is exemplified by the use of a long chain fatty acid such as caprylic acid to stabilize albumin during heating. However, since different proteins bind different ligands, the addition of a ligand which stabilizes one protein does not necessarily stabilize another.

It should be emphasized that proteins derived from the same tissue (e.g. blood) or even the same cell may exhibit marked differences in thermal stability. For example, plasma protein Factor VIII is very rapidly inactivated when heated in solution at 60 degrees C. while, as noted above, albumin may survive such temperature when stabilized with certain fatty acids. This illustrates the fact that the optimum conditions for protein stabilization cannot be predicted on the basis of protein source.

With regard to hemoglobin stability the extant literature is particularly confusing and often conflicting. Hemoglobin has long been known to be susceptible to oxidation to the met form in which heme iron is in the ferric ($+3$) form rather than the normal ferrous ($+2$) state. Methemoglobin does not reversibly bind oxygen and is therefore non-functional as an oxygen carrier. It is also less stable in solution. It is therefore universally accepted that a useful hemoglobin-based oxygen carrying solution should contain low amounts of methemoglobin, but despite years of intense study the precise mechanism by which hemoglobin oxidizes is not yet known. In general, however, hemoglobin solutions which are stored cold or even frozen oxidize less rapidly than those stored at higher temperatures (Iorio, Methods in Enzymology (1971) 76:57-71). Thus, in general, researchers attempting to preserve hemoglobin structure and function avoid high temperatures.

The relationship between oxygen and hemoglobin stability is complex and the literature contradictory. Kikugawa et al., (Chem. Pharm. Bull. (1961) 29:1382-1389) claims that deoxyhemoglobin was more stable than oxyhemoglobin during incubation at 37 degrees C., and Rieder (J. Clin. Invest. (1970) 49:2369-2376) and Winterbourn and Carrel (J. Clin. Invest. (1974) 54:67-689) have asserted that deoxyhemoglobin heated in an evacuated vessel is more heat stable than oxyhemoglobin heated under ambient oxygen partial pressure. Muller and Schmid reported that deoxyhemoglobin denatured at a higher temperature than oxyhemoglobin when both were heated in a calorimeter. On the other hand, Mansouri and Winterhalter (Biochemistry (1973) 12:4946-4949) have noted that in their experiments lowering the oxygen pressure increased the rate of autoxidation. Banerjie and Stetzkowski (Biophys. Acta (1970) 22:636-639), Wallace et al., (J. Biol. Chem. (1982) 257:4966-4977), and Brooks (Proc. Royal Soc. London B (1935) 118:56-577) have also noted a similar phenomenon, leading several of these researchers to propose that it is actually the deoxygenated hemoglobin which preferentially undergoes conversion to the met form. Eyer and coworkers (Mol. Pharmacol. (1975) 11:326-334) found that methemoglobin formation by hydrogen peroxide was much higher when the oxidant was infused into solutions of deoxyhemoglobin as opposed to the oxygenated protein. Part of this complexity stems from the fact that oxygen is both a ligand which can reversibly associate with hemoglobin and a reactant which may oxidize the protein.

The complexity of hemoglobin stability is further illustrated by the reported effects of antioxidants and reducing agents. The antioxidant ascorbic acid has been shown to both reduce methemoglobin (Gibson, Biochem. J. (1943) 37:615-618) and to oxidize oxyhemoglobin (Harvey and Kanek, Brit. J. Haematol. (1976) 32:193-203). Reduced glutathione is another antioxidant which induces methemoglobin formation when added to solutions of purified hemoglobin, even though it is believed to function as a protective agent for hemoglobin in vivo (Sampath and Cuaghey, J. Am. Chem. Soc. (1985) 107:4076-4078). In point of fact, many reducing agents are known to enhance methemoglobin formation even though others exhibit the expected ability to reduce the oxidized protein (Eyer et al., in *Biochemical and Clinical Aspects of Hemoglobin Abnormalities* (1978) Academic Press, New York, pp. 495-503; Kawanishi and Caughey in *Biochemical and Clinical Aspects of Oxygen* (1979) Caughey W.S. ed, Academic Press, New York, pp. 27-34). This behavior apparently occurs because, in addition to being able to directly reduce methemoglobin, reducing agents may also generate peroxides when they are oxidized in other reactions. Thus, the net effect of adding a particular reducing agent depends on which other enzymes and reactants are present as well as the oxidation reduction potential of the reducing agent.

Antioxidants have been used in association with hemoglobins in the past. Hollocher, "J. Biol. Chem" 241:9 (1966) observed that thiocyanate decreases the heat stability of hemoglobin.

European Patent Application 78961 teaches stabilizing crosslinked hemoglobin against oxidation by the use of an antioxidant.

Daland et al., "J. Lab. Clin. Med." 33:1082–1088 (1948) employs a reducing agent to reduce red blood cell hemoglobin in order to assay for sickle cell anemia.

Sodium ascorbate was disclosed to be ineffective in protecting the hemoglobin molecule from deterioration during prolonged storage. Rabiner et al., "Ann. Surg." 171:615 (1970).

Hemoglobin solutions have been proposed for use as blood substitutes, either as a solution of crystalline hemoglobin or as a polymer crosslinked to other hemoglobin or other macromolecules such as polysaccharides. See for example U.S. Pat. Nos. 4,001,401; 4,061,736; 4,053,590; and 4,001,200; and West German Offenlugungsschriften 3029307 and 2616086. All of these products are obtained by processes which use human red blood cells from whole blood cells as a starting material. The hemoglobin is separated from the formed matter (including stroma) of the red cells by lysis and centrifugation, followed by processing in accordance with known techniques, including substitution with pyridoxal groups. These methods are not concerned with assuring that any viruses present in the whole blood are removed.

Taken as a whole, the prior art suggests only that hemoglobin stability is a complex function of solution composition, pH and temperature with no indication as to whether or how a solution of hemoglobin might be heated to 60 degrees C. or more for a prolonged period of time. This is evidently the reason why the successful heating of hemoglobin solutions for the purpose of inactivating viruses has never been attempted, despite the immense amount of research which has been performed on hemoglobin structure and function, and the intense interest in the use of the protein in the formulation of oxygen carrying intravenous solutions. Surprisingly, I have discovered a set of conditions under which hemoglobin may be heated at temperatures of 60 degrees C. or more for 10 or more hours with little loss of structural integrity or oxygen transport capacity, making possible the heat-inactivation of virus in hemoglobin, whether crosslinked or otherwise.

Another problem in the development of a hemoglobin based oxygen transport solution is the purification of the hemoglobin. Commonly used methods for the obtaining of partially purified hemoglobin solution (so called "stroma-free hemoglobin") employ cell lysis with solvents or by exposure to hypotonic conditions, followed by the removal of membrane fragments by filtration, centrifugation and/or precipitation under acidic conditions. See for example (Rabiner et al., Ann. Surg. (1970), 171:615–622; Feola et al., Surg. Gyn. Obstet. (1983), 157:399–408; Bonsen et al., (1977) U.S. Pat. 4,001,401; and Bonhard (1975) U.S. Pat. No. 3,864,478. While these procedures remove substantial amounts of the cell stroma they do not effectively remove many of the contaminating soluble proteins. If one wishes to modify the hemoglobin chemically, especially with nonspecific reagents such as glutaraldehyde, the presence of intracellular proteins results in a variety of by-products which complicate subsequent purification, reduce yields and increase the probability of product toxicity. To mitigate such problems, researchers have frequently purified hemoglobin by various chromatographic techniques. Although these techniques are capable of effective purification, they are often laborious and require the use of expensive chromatographic media which are difficult to sterilize and depyrogenate. Other purification techniques, such as electrophoresis or ultra-centrifugation, are not amenable to large scale production. In the present invention, a substantial purification is achieved by means of a simple heating process which can be readily performed in large scale production with equipment which is easily sterilized and depyrogenated. Therefore, by this invention one may purify hemoglobin solutions through selective removal of nonhemoglobin proteins without denaturing a substantial portion of the hemoglobin so that it becomes incapable of performing its oxygen transport function in vivo.

The term "hemoglobin" as used herein is generic for oxy-, carboxy-, and deoxyhemoglobin, as well as pyridoxalated (covalently bonded to pyridoxal groups by reaction with pyridoxal-5'-phosphate) and/or crosslinked derivatives thereof unless otherwise stated. Crosslinked derivatives include glutaraldehyde, ring-opened diol, and 3,5-dibromosalicyl-bis-fumarate (DBBF) crosslinked hemoglobin, among others. These hemoglobin derivatives are well-known.

SUMMARY OF INVENTION

I have now discovered a method for reducing the risk of biologically infectious virus in hemoglobin-containing compositions, and removing heat precipitable nonhemoglobin proteins, which comprises: heating a substantially cell-free hemoglobin solution at a temperature of 45 degrees to 85 degrees C., while maintaining said hemoglobin in substantially its deoxyhemoglobin form, to inactivate virus present without substantially inactivating said hemoglobin. Additionally or alternatively, the same method can cause certain nonhemoglobin proteins to be selectively precipitated, also without substantially biologically inactivating the hemoglobin. This method may be used to accomplish either or both of the above purposes of viral inactivation and precipitation of nonhemoglobin protein. Hemoglobin may be deoxygenated by any desired means.

In one embodiment, the hemoglobin solution may be deoxygenated by admixture with a chemical reducing agent which causes the hemoglobin to be converted and maintained in its substantially deoxyhemoglobin form and heated in the presence of this reagent. Alternatively, the hemoglobin may be converted into and maintained in its substantially deoxyhemoglobin form and heated in the presence of such a reducing agent. Preferably, the hemoglobin may be converted into and maintained in its substantially deoxyhemoglobin form by exposure to inert, essentially oxygen free gas or vacuum, to cause removal of oxygen from the hemoglobin and conversion of other forms of hemoglobin to deoxyhemoglobin. One maintains the deoxyhemoglobin in an oxygen-free environment during the above-described heating, for accomplishing either or both of the above purposes. Specifically, the hemoglobin may be exposed to such gas or vacuum through an oxygen permeable, hemoglobin-retaining membrane, as described for example in the article by Robert Schmukler et al. *Biorheology*, (1985) 22:21–29.

More specifically, one may pass a solution of the substantially cell-free hemoglobin through diffusion cell means, the diffusion cell means having membrane wall means along which the hemoglobin solution flows, such membrane wall means being capable of passing oxygen but not hemoglobin through the membrane wall means, while circulating inert gas along the side of the membrane wall means opposed to the hemoglobin solution, to cause removal of oxygen from the hemoglobin solution and conversion of other forms of hemoglobin to deoxyhemoglobin. One then heats the resulting deoxyhemoglobin solution at essentially 45 degrees to 85 degrees C. in an oxygen-free environment to inactivate virus present and/or to precipitate heat-precipitatable nonhemoglobin proteins without substantially inactivating the hemoglobin.

Preferably, the flow volume of circulating, inert gas is at least 5 times the flow volume of the hemoglobin solution passing through the diffusion cell means, and, most preferably, from about 10 to 50 times the flow volume thereof, although there really is no significant upper limit to the flow volume of circulating, inert gas that may be used apart from economic considerations. Typically, the circulating, inert gas may be nitrogen or argon, and the heating temperature may be from about 45–50 degrees C. to 85 degrees C. For example, a time of heating of about 10 hours at about a temperature of about 60 degrees C. can provide excellent results both in the precipitation of nonhemoglobin proteins and in the inactivation of virus in hemoglobin solutions in accordance with the process of this invention.

Prior to heating, the pH of the solution is preferably adjusted to between 6.0 and 9.0 to inhibit methemoglobin formation and hydrolysis. One then heats the resulting deoxyhemoglobin solution at preferably essentially 55 degrees to 80 degrees C. in an oxygen-free environment to inactivate virus present and/or to precipitate nonhemoglobin proteins without substantially inactivating the desired hemoglobin derivative. More specifically, a time of heating of about 8 to 12 hours, for example 10 hours, at about a temperature of about 60 to 75 degrees C. can provide excellent results both in the precipitation of nonhemoglobin proteins and in the inactivation of virus in hemoglobin solutions in accordance with the process of this invention.

DETAILED DESCRIPTION OF THE INVENTION

Biologically active hemoglobin is hemoglobin which is capable of performing in vivo or in vitro the oxygen transport function of native hemoglobin. However, it is not necessary for the hemoglobin to function with the efficacy found in its red blood cell environment. Rather, a comparison is made between the material without the heat treatment herein and a comparable lot after such heat treatment. This comparison can be made with in vivo or in vitro assays already known in the art, for example measurement of arteriovenous oxygen differences in the rat after exchange transfusion with the test composition, by changes in the absorption spectrum of the hemoglobin before and after treatment, or by direct determination of the oxygen binding characteristics of heated and unheated hemoglobin. Hemoglobin that is biologically inactive, for example, may have been converted to methemoglobin, had its protein component denatured, or has been otherwise adversely impacted by heat or other means.

Hemoglobin compositions include the hemoglobin derivatives discussed above, native, substantially purified hemoglobin, or crude red blood cell hemolysates. Ordinarily one will not be interested in methemoglobin or its derivatives because they are not biologically efficacious.

Suitable hemoglobin compositions may contain at least 99% hemoglobin by weight of total protein, a total phospholipid content of less than about 3 ug/ml, less than about 1 ug/ml of either phosphatidylserine or phosphatidylethanolamine, an inactive heme pigment of less than 6%, an oxygen affinity (P50) of about from 24 to 28 mm. Hg (37 degrees C., pH 7.4, pCO2 of 40 mm. Hg, and 1 mM hemoglobin) with a Hill's constant of at least about 1.8 and an oxygen combining capacity of at least about 17 ml. 02/dl. of hemoglobin solution. These specifications are not critical; others may be employed.

A preferred hemoglobin composition for processing in accordance with this invention may be an aqueous solution containing 5 to 15 g./dl. of hemoglobin which is cross-linked predominantly between the alpha chains by reaction with the diaspirin reagent 3,5-dibromosalicyl-bis-fumarate, with an inactive heme pigment content of less than 6 percent, a P50 under physiologic conditions of at least 26 mm. Hg, and containing electrolytes at concentrations of 100–160 mmoles/L sodium chloride, 3 to 5 mmoles/L potassium chloride, 0 to 30 mmoles/L sodium lactate, 0 to 25 mmoles/L sodium pyruvate, 0 to 30 mmoles/L sodium bicarbonate, and 0 to 2 mmoles/L magnesium chloride, at a pH of 7.25 to 7.45 at 37 degrees C..

One such preferred solution of the above described hemoglobin is present in solution at a concentration of 14 g./dl., having less than 6 percent inactive heme pigment, and exhibiting a P50 of 32 mm. Hg under physiologic conditions. Such a preferred solution contains about 100 mmoles/L sodium chloride, 4 mmoles/L potassium chloride, 10 mmoles/L sodium lactate, 20 mmoles/L sodium pyruvate, 0.5 mmole/L calcium chloride, and 0.25 mmole/L magnesiuim chloride. The pH of the solution at 37 degrees C. may be 7.4

The hemoglobin composition generally will be dissolved in water or buffer solution at a concentration of about from 1 to 40 g/dl, preferably about from 1 to 14.5 g/dl prior to heat treatment. The concentration selected will depend upon whether the solution is intended to be used as such for therapeutic use or to be further processed by ultrafiltration and the like, or lyophilized. In the latter situation the concentration can be any that is conveniently handled in the subsequent processing steps. Where the product is to be infused it may have a concentration of about from 13.5 to 14.5 grams of hemoglobin composition per dl.

Stroma-free hemoglobin solutions which are useful in this invention can be prepared using conventional techniques. Such techniques include, but are not limited to, those disclosed in U.S. Pat. No. No. 4,401,652 to Simmonds et al., European Patent Application No. 82106849.1 to Bonhard et al., Cheung et al., Anal. Biochem. (1984) 137:481–484 and De Venuto et al., J. Lab. Clin. Med. (1977) 89:509–516. Other methods of preparing such solutions will be apparent to those skilled in the art.

The heat treatment step can be performed before or after chemical modification of hemoglobin, as long as the hemoglobin is in the deoxy form.

The hemoglobin composition generally will be dissolved in water at a concentration of about from 0.001 to 40 g/dl, preferably about from 0.03 to 3 g/dl or 1 to 14 g/dl prior to heat treatment. The concentration selected will depend upon the ability to deoxygenate the solution while maintaining adequate pH control as well as the available or desired hemoglobin concentration for previous or subsequent process steps, respectively.

As noted above, deoxygenation may be effected by chemical or physical means. If a reducing agent is used it should be capable of fully converting hemoglobin to the deoxy form either before or during, but preferably before, heating without inducing substantial methemoglobin formation. I have found that ascorbate is relatively ineffective in heat stabilizing hemoglobin for the purposes herein. Thus the reducing agent should have a greater or more effective reducing potential than ascorbate. Reduced redox dyes and sulfhydryl or sulfoxy compounds include many acceptable agents. Suitable reducing agents are alkali metal dithionite, bisulfite, metabisulfite or sulfite, reduced glutathione and dithiothreitol. Dithionite is preferred. Other preferred reducing agents which give an intermediate level of protection are compounds which induce hemoglobin deoxygenation during, but not prior to, heating. These include, but are not limited to, reduced glutathione, N-acetyl-L-cysteine and N-2-mercapto-propionyl glycine. Other appropriate agents will be easily determined by routine experiments as described in Example 1 below.

The quantity of reducing agent to be included in the aqueous solution of the hemoglobin composition will vary depending upon the reducing strength of the agent, the quantity of hemoglobin, the estimated viral burden and/or quantity of nonhemoglobin proteins (and, as a consequence, the intensity of the heat treatment), the presence of oxidizing solutes and oxygen, the necessity for proper pH control, and other factors as will be apparent to the skilled artisan. Accordingly, the optimal concentration will be determined by routine experiments. This can be done by following the in vitro changes in the hemoglobin U.V.-visible spectrum as described below in Example 2 and in FIG. 1, to assure that only sufficient reducing agent is included to preserve a substantial proportion of the biological activity of the hemoglobin under the viral inactivation conditions or the like, but no more than that amount. The amount of dithionite which can be added is limited by the propensity of this agent to generate acid equivalents upon reaction with oxygen. The solution must be adequately buffered to prevent the pH from dropping below 6.0. Since dithionite must be added in excess of the amount of oxygen, and thus hemoglobin, in the system, there is a complex relationship between the concentration of hemoglobin, buffer, and dithionite. A useful combination of these parameters is a hemoglobin concentration of 1-9. g/dl., dithionite concentration of 10-100 mM, and a sodium phosphate buffer concentration of 100mM.

Various additives may be present in the composition in addition to the reducing agent, for example, buffers such as phosphate, bicarbonate or tris (to pH of about 7-8), inorganic ions in concentrations generally less than or equal to that found in plasma (e.g., sodium, chloride, potassium, magnesium, and calcium chloride at concentrations of typically no more than about 150 meq/l each) and lyophilization stabilizers such as amino acids or saccharides. One may use non-reducing sugars such as mannose or sugar alcohols when lyophilized hemoglobin compositions are heat treated. The concentration of additives in the hemoglobin solution can vary, depending upon the effect upon hemoglobin stability. For example, when sodium phosphate (pH 7.4) is utilized as a buffer, concentrations above 70 mM result in a decrease in hemoglobin stability. This would suggest that hemoglobin stability is reduced in hypertonic media. The pH of the solution can also vary depending upon the identity of the reducing agent, additives and heat treatment conditions. The pH can range from 6.0 to 9.0. Preferred ranges are from about 7.0 to about 8.5. The most preferred pH is from about 7.4 to about 7.6.

Hemoglobin can also be maintained in the deoxy form using various solution degassing procedures. These include, but are not limited to, deoxygenation by means of circulation of the hemoglobin solution through a membrane gas exchange device which is concurrently flushed with an inert gas such as nitrogen as described, for example, by Schmukler et al. (Biorheology (1985) 22:21-29,), exposure of solution to vacuum, and/or sparging inert gas through the solution using, for example, known designs of blood bubble oxygenators as described in U.S. PatNos. 3,892,534 or 3,792,377. The suitability of such procedures will be limited by the extent they promote degradation of hemoglobin through foaming, acidification, etc. Foaming may be controlled by adding compatible defoaming agents to the solution, such as caprylic alcohol, if such agents do not adversely effect heat stability. Alternatively, mechanical defoaming devices can be used to mitigate this problem. Mechanical deoxygenation may also be used in conjunction with chemical reductants such that the concentration of the latter required to effect complete deoxygenation is reduced.

The time and temperature of treatment will depend on a number of factors such as viral burden, protein concentration, nature of hemoglobin (i.e. crosslinked or not), and the desirability of precipitating unmodified hemoglobin. The first nonhemoglobin proteins typically precipitate within 30 minutes to 1 hour at about 60 degrees C. As heat treatment continues, more nonhemoglobin proteins precipitate. In a preferred embodiment wherein viral burden is also reduced, heat treatment is continued to about 10 or 15 hours. Purification of the solution may typically proceed until a reduction of at least 20 percent and preferably at least 50 percent by weight of nonhemoglobin proteins has been achieved. This can be accomplished by the method herein without a substantial loss of hemoglobin biological activity; i.e. only about from 1 to 15 mole percent of hemoglobin is rendered inactive in the ordinary case. The temperature of heat treatment will range typically about from 45 degrees C. to 85 degrees C., typically 50 to 80 degrees C., preferably about 60-66 degrees C., if the inactivation is to occur over a reasonably brief period of time. The time typically will range about from 1 to 30 hours, but optionally up to 150 hours, preferably 2-10 hours for solutions. The shorter incubation will be used with higher temperatures. The heat treatment of the deoxygenated hemoglobin solution may be effected by any method for heating such as microwave or infrared radiation, or thermal contact by such devices as resistance heaters or water baths.

The temperature of the composition is typically increased in a manner to avoid localized overheating, up to a viral inactivating and precipitating temperature. The heating time will range typically from about 20 to 96 hours for dry compositions. The time and temperature of inactivation will depend upon a number of factors such as the viral bioburden, the protein concentration, the nature of the hemoglobin (crosslinked or not) and the reducing agent concentration (when present).

The efficacy of the treatment process for viral kill is best assayed by seeding an aliquot of the composition to be treated with a candidate virus such as sindbis, cytomegalovirus or T4. Suitable methods for such assays are disclosed in PCT publication WO 82/03871. The reducing agent concentration (when used) and the time and temperature of candidate virus inactivation are balanced against the loss of hemoglobin biological activity, to arrive at the optimal conditions for heat inactivation. The inactivation of candidate virus should proceed until a reduction of at least 3, and preferably 6, logs of viral activity has been achieved. This can be accomplished by the method herein without a substantial loss in hemoglobin biological activity, i.e., only about from 1 to 15 mole percent of hemoglobin is biologically inactive.

The resulting product will contain biologically active hemoglobin; will be substantially free of biologically inactive hemoglobin; and will be free of biologically infectious virus. The residues of biologically noninfectious virus may be detected by immune assays for viral antigens, since these antigens may not be immunologically destroyed by the process. However, viral infectivity assays will demonstrate that virus inactivation has occurred. The presence of viral antigens coupled with a loss in or substantial lack of viral infectivity is an indicia of products treated in accord with this process, where viral inactivation is desired.

Heat treated solutions may be processed in order to make them convenient for therapeutic use. Dilute hemoglobin solutions may be concentrated by ultrafiltration and/or lyophilization.

Ultrafiltration is useful also if necessary to remove excess reducing agent when present, i.e. to reduce the concentration of reducing agent to a physiologically acceptable level. This will ordinarily be on the order of less than about 5 mM, but the exact amount will depend on the estimated rate of infusion and the character of the reducing agent. For example, reduced glutathione is relatively innocuous and may retain in the composition in relatively high proportions.

The heat treatment step can be performed before or after the pyridoxalation or cross-linking referred to above. Preferably the hemoglobin is pyridoxalated and crosslinked before heat treatment. This helps to ensure that any viral contamination which may occur during manufacturing is also dealt with. If the amount of reducing agent used during heat treatment is physiologically acceptable, then the heating can occur in final filled containers such as bags or vials.

The hemoglobin composition is advantageously in aqueous solution when heat treated, but dry composition also can be heat treated. For example, if the hemoglobin composition is intended for long-term storage it may be lyophilized or dried from a solution containing the reducing agent, and then heated.

Stroma-free hemoglobin solutions which are useful in this invention can be prepared using conventional techniques. Such techniques include, but are not limited to, those disclosed in U.S. Pat. No. 4,401,652 to Simmonds et al., European Patent Application No. 82106849.1 to Bonhard et al., the Cheung et al. article, "The Preparation of Stroma-free Hemoglobin by Selective DEAE-Cellulose Absorption," Analytical Biochemistry 137 pp. 481–484 (1984) and De Venuto et al., "Characteristics of Stroma-Free Hemoglobin Prepared by Crystallization," J. Lab. Clin. Med. 89:3, p. 509–516 (1977). Other methods of preparing such solutions will be apparent to those skilled in the art.

For the purposes of this invention the reducing agent, when used, may be a substance or chemical or physical intervention that prevents hemoglobin denaturation by maintaining the hemoglobin in the deoxy form during heating. Reducing agents comprises chemireductants which convert hemoglobin to the deoxygenated form. Preferred agents convert oxyhemoglobin to the deoxy form without consistent methemoglobin formation.

As stated above, hemoglobin can also be maintained in the deoxy form using various solution degassing procedures. These also include but are not limited to bubbling with nitrogen gas, sparging with inert gases, and exposing solutions to a vacuum. The suitability of such procedures will be limited by the extent that they promote degradation of hemoglobin, e.g. through foaming, acidification, etc.

The concentration of hemoglobin preferably present in solution will vary dependent upon the identity of the reducing agent utilized and subsequent processing steps. Where the reducing agent is a chemireductant, the concentration of hemoglobin will generally vary from about 0.001 to about 40 g/dl. The preferred concentration ranges from about 0.03 to 3 and up to about 14 g/dl. For example, if sodium dithionite is the reducing agent and greater concentrations of hemoglobin are used, the amount of dithionite which must be added to sustain the unoxidized state may cause the solution to become too acid. In such cases, the probability of nonspecific precipitation may be increased. If the reducing agent is a physical intervention, e.g. sparging or diffusing with inert gas, the acidity problem is eliminated. Under such circumstances hemoglobin concentrations can range from about 0.001 to about 30 g/dl.

The following examples are intended to be illustrative, and should not be construed as limiting the scope of the invention.

EXAMPLE 1

This contemplated procedure is illustrative of the manner in which hemoglobin compositions may be treated in accord with this invention. A solution is prepared which contains 1 g % stroma-free hemoglobin, 30 mM of sodium dithionite and sufficient sodium bicarbonate buffer (0.1 to 0.3M) to maintain the pH at 7.5. One hundred ml. of this solution is sealed in a glass vial so as to leave no gas lead space, and then heated at 60 degrees C. for 10 hours by immersion in a water bath. After heating, the solution is removed from the bath. After heating, the solution is removed from the vial, diafiltered over a 30,000 MW cutoff membrane to remove excess dithionite and to adjust the ionic content of the medium, concentrated by ultrafiltration to a hemoglobin content of 14 g/dl, and passed through a 0.2 micron filter to remove any particulate matter and to remove bacteria.

EXAMPLE 2

Figure 1:
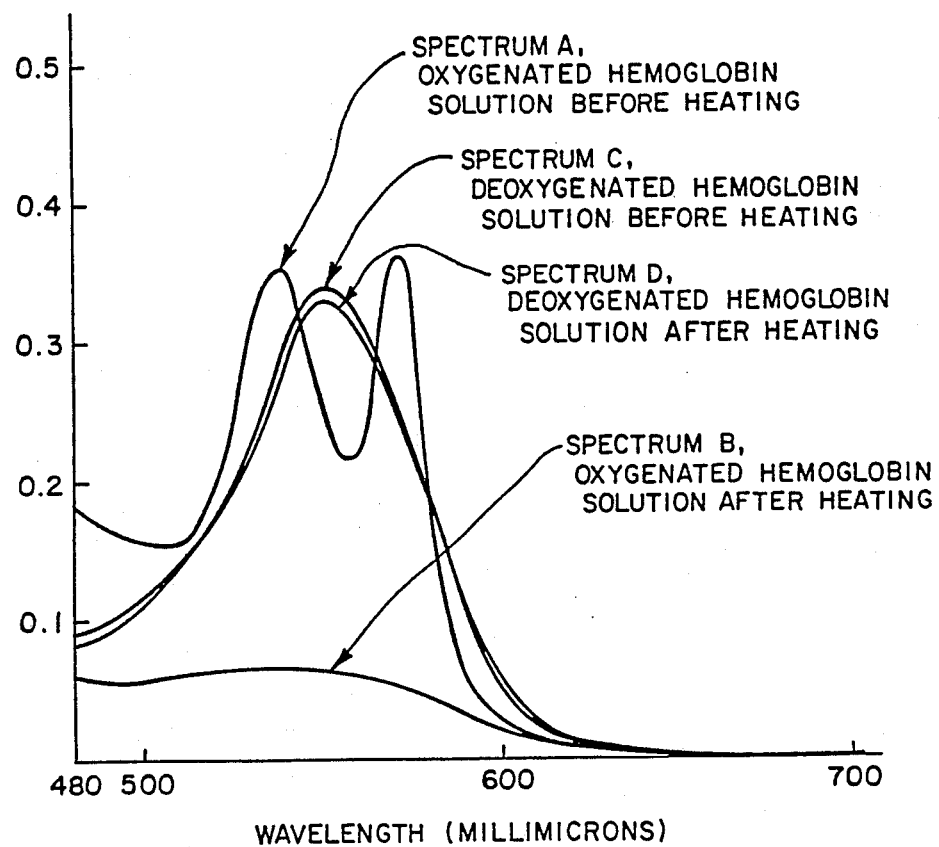
FIG. 1 is a graph which discloses the stabilizing effect of the deoxy form of hemoglobin deoxygenated by dithionite reducing agent in hemoglobin after heating in solution at 56 degrees C. for 10 hours.

Two aliquots of stroma-free hemoglobin solution prepared as above were diluted to a concentration of 0.04 g/dl in 0.1 M sodium phosphate buffer solution, pH 7.4. One aliquot was admixed with sufficient sodium dithionite to give a final concentration of 92 mM and quickly sealed into a glass vial with no headspace. The other aliquot was sealed into a similar vial but without the added dithionite. Absorption spectra over the range of 400–700 nanometers were taken of both samples directly from the vials. These spectra revealed that the sample containing dithionite was completely deoxygenated (as shown in FIG. 1) whereas the other sample exhibited a typical oxyhemoglobin spectrum. Both samples were incubated at 56 degrees C. for 10 hours and, after cooling to room temperature, absorption spectra were again taken. These spectra revealed that the hemoglobin in the deoxygenated sample was virtually unchanged, as shown in FIG. 1, whereas the absorption spectrum of the oxygenated sample was indicative of a highly degraded sample. When the sample heated in the deoxy state was dialyzed to remove the dithionite a normal oxyhemoglobin spectrum was obtained. Thus, biological activity of the hemoglobin was retained during heating in the deoxy, but not the oxy, state.

EXAMPLE 3

The procedure of Example 1 is repeated in this contemplated example with the heated test composition containing reductant. This composition was divided into 3 aliquots which respectively were seeded with sinbis, encephalomyocardities (EMC), and adeno type 5 virus so that the concentration of virus was, respectively, 6–7 log 10 plaque forming units (PFU)/ml, 4 log 10 PFU/ml and 4.5 log 10 tissue culture 50% infective dose (TCID-50)/ml.

The TCID designation may be explained as follows: In biological quantitation, the end point is usually taken as the dilution at which a certain proportion of the test system cells react or die. The 100% end point is frequently used. However, its accuracy is greatly affected by small chance variations. A desirable end point is one representing a situation in which one-half of the test system reacts while the other one-half does not. The best method is to use large numbers of test systems at closely spaced dilutions near the value for 50% reaction and then interpolate a correct value. The negative logarithm of the TCID end point titer is:

$$\begin{pmatrix} \text{Negative log.} \\ \text{of highest} \\ \text{virus} \\ \text{concentration} \\ \text{used} \end{pmatrix} - \left[ \left( \frac{\text{Sum of \% morality at each dilution}}{100} - 0.5 \right) \times \begin{matrix} \text{logarithm} \\ \text{of} \\ \text{Dilution} \end{matrix} \right]$$

The tissue culture 50% end point represents a viral titer that gives rise to cytopathic changes in 50% of the cells in an inoculated culture. In applying the above technique for determination of concentration, logarithmic dilutions are prepared in minimum essential medium plus 2% fetal calf serum. 0.2 ml of each dilution is added to replicate cultures of BGMK (Buffalo Green Monkey Kidney) cells in microtiter plates. The inoculated cultures are incubated at 36 degrees C. under 5% carbon dioxide and observed microscopically over a period of 7 to 8 days. The percent mortality of cells in a culture at a given dilution is determined by observing for cellular degeneration, as evidenced by refractile cells. The TCID-50 can then be calculated as shown above.

The EMC and sindbis virus infective titer is obtained by preparing dilutions of viral suspension as described above. BGMK cell monolayers were prepared in 35 mm petri dishes. Viral adsorption to the cells was initiated by adding 0.2 ml of suspension to the monolayer. After 1 hour, the monolayer was overlaid with 2 ml of nutrient agar medium and incubated for 24–72 hours at 37 degrees C. The plaques which formed were then made visible by staining the cells with neutral red at 1:2000 by weight in saline.

The results with virus were subjected to regression analysis with the method of least squares to allow the fitting of a linear line to the data and plotted. Similar results were obtained with all viruses. The viral infective titer in all three aliquots was reduced significantly by the method of heat treatment, thereby reducing the risk of patient infection by hepatitis or other viruses.

EXAMPLE 4

The method of Example 1 was repeated in this contemplated example except that the stroma-free hemoglobin had been crosslinked by 3.5-dibromosalicyl-bis-fumarate and subsequently pyridoxalated in accord with the method disclosed by Tye et al., in Bolin et al., editors, Advances in Blood Substitute Research, New York, Alan R. Liss, (1983) and literature cited therein.

EXAMPLE 5

An aliquot of stroma-free hemoglobin (SFH) containing 8 g/dl SFH and prepared by standard techniques was diluted with seven volumes of isotonic sodium phosphate buffer solution, pH 7.4, to give a solution (1 g/dl) in SFH. Sodium dithionite was added to this solution to give a final concentration of 8.7 mg/ml and the pH adjusted to 7.5 with sodium hydroxide. This solution was then sealed into airtight containers which were heated at 60 degrees C. for 10 hours. After cooling to room temperature, the solutions were centrifuged at 5000 x g. for 5 min. and the supernatant recovered and respun to remove any residual particulate matter. The pellet resulting from the original centrifugation was washed five times in isotonic sodium phosphate buffer, pH 7.4, and finally resuspended in a minimum volume of the same buffer solution. Aliquots of the SFH solution before heating, the supernatant obtained after heating and centrifugation, and the washed precipitate obtained after heating were solubilized in 1.5% SDS containing 1 mg/ml dithiothreitol and analyzed by polyacrylamide gel electrophoresis. The results of this analysis demonstrated that the level of impurities was reduced in heated SFH solutions as compared to the original unheated solution and that the pellet consists predominately of impurity proteins.

EXAMPLE 6

In this example, stroma-free oxyhemoglobin solution is treated physically, rather than chemically, to exchange dissolved oxygen from the solution with physiologically inactive gas to remove oxygen from the oxyhemoglobin molecule, prior to heating in a manner previously described to inactivate virus and to precipitate nonhemoglobin proteins as desired. The present approach provides a gentle and biocompatible process for relatively rapid and complete deoxygenation of hemoglobin with conservation of its biological activity (i.e. formation of little or no methemoglobin).

Figure 2:
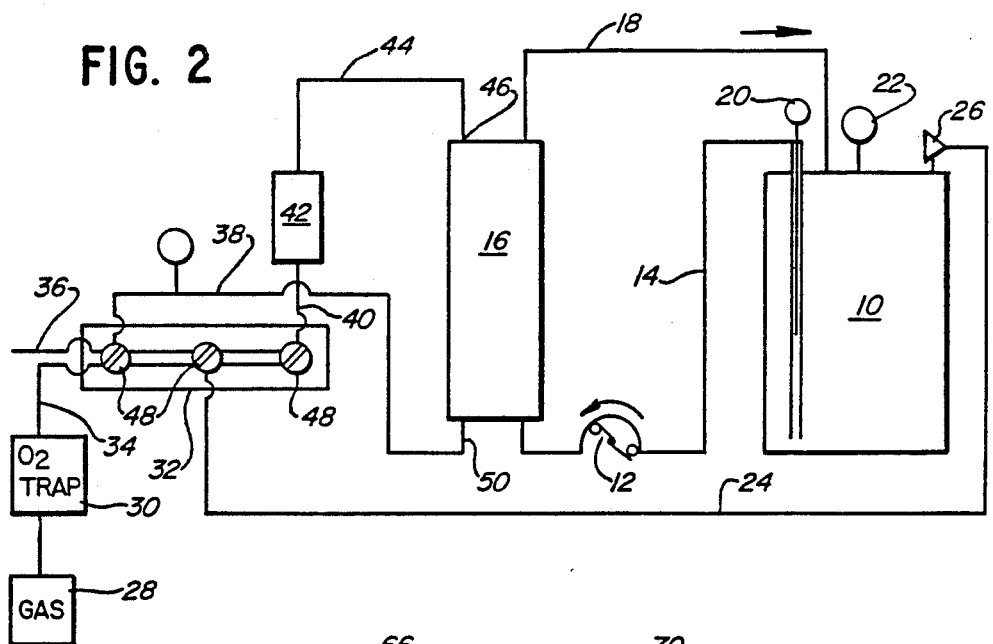
FIG. 2 is a schematic view of apparatus for deoxygenating hemoglobin solutions.

Referring to FIG. 2, a typical apparatus for deoxygenating hemoglobin is shown in schematic form. Hemoglobin solution is placed in dispensing vessel 10. A conventional roller pump 12 pumps the hemoglobin solution through line 14 to one end of a membrane oxygenator 16, for example a Model No. 08-2A of Sci-Med Life Systems, Inc. of Minneapolis, Minn. After passing through the membrane oxygenator (which is used as a diffusion device herein, not as an oxygenator) the hemoglobin solution returns to dispensing vessel 10 through line 18.

A temperature probe 20, pressure gauge 22, and vacuum-gas line 24 may connect to vessel 10, with line 24 being controlled by relief valve 26. This permits the evacuation of dispensing vessel 10 through line 24 to remove oxygen from the vessel.

Oxygen-free gas, for example, nitrogen or argon, may be delivered from gas source 28 through a conventional oxygen trap 30 into multiple way valve 32 by line 34. Vacuum line 36 connects to any conventional vacuum source, to provide suction to line 24, and also to vacuum line 38 which communicates with the outlet of the gas side of membrane oxygenator 16. Gas line 34, in turn, may communicate through multiple way valve 32 to line 40, which passes through flow meter 42 and line 44 to the gas entry port 46 of oxygenator 16. Thus, by appropriate control of multiple way valve 32, oxygen gas may be removed from vessel 10, and then gas from source 28 may be directed through oxygenator 16 in its gas side in counter current manner to the flow of hemoglobin solution on the liquid side of oxygenator 16. Hence, by a diffusion process, the hemoglobin in the solution is deoxygenated to deoxyhemoglobin.

Following the deoxygenation process, dispensing vessel 10 may be disconnected from the rest of the system without permitting the entrance of oxygen, and heated in accordance with conditions described above, typically in the absence of any added chemical reducing agents, to inactivate virus in the hemoglobin solution, and to precipitate nonhemoglobin proteins.

Oxygen trap 30 may be Oxiclear Model No. DPG-250 of LabClear of Oakland, California. The multiple way valve 32 may be one sold by Kontes Glass Co. of Vineland, New Jersey, with added stopcocks 48 being from the Rotaflo Company of England. Other components may be of conventional design and are commercially available.

One may deoxygenate and pressurize dispensing vessel 10 by pumping gas from source 28 into the dispensing vessel. This can be accomplished by appropriate control of multiple way valve 32 and roller pump 12, followed by evacuation of container 10. One may then impose a vacuum on the gas side of membrane oxygenator 16 up to about minus 20 inches of mercury, then adjusting the flow of gas from source 28 through the oxygenator to the desired selected flow rate. The flow of hemoglobin solution from dispensing vessel may be pressurized up to about +5 psi. with this condition remaining throughout the deoxygenation procedure.

The course of deoxygenation may be monitored by sampling hemoglobin solution through a flow cuvette.

(A) In this particular procedure, making use of the described apparatus of FIG. 2, one liter of stroma-free oxyhemoglobin solution containing one gram of oxyhemoglobin per deciliter, a pH of 7.0, and buffered with 10 millimolar sodium phosphate solution was allowed to flow through membrane device 16, having a membrane area area of 0.8 square meter, and into dispensing vessel 10, which had a capacity of 10 liters. Vessel 10 was deoxygenated in the manner described above and slightly pressurized with nitrogen (+35 kPa).

The solution was then circulated through the system by peristaltic pump 12 at a rate of 150 ml./min. while oxygen-free nitrogen was passed through the gas side of membrane oxygenator 16 at a rate of 2,000 ml./min., with a vacuum of −500 mm Hg being applied at gas outlet 50 of membrane device 16. This ratio of gas to hemoglobin solution flow was kept relatively constant at 13 to 1 throughout the procedure.

During the process, samples were taken from the system under nitrogen blanket, and the absorbances and spectra were recorded using a flow-through cuvette having a 0.2 cm. path length. The results are presented in Table I below, and indicate that complete deoxygenation (99.7%) was achieved after 60 minutes of circulation:

TABLE 1

| Deoxygenation Time (Min.) | % Oxy-hemoglobin | % Deoxy Hb | % Met Hb | % Hb Saturation |
|---|---|---|---|---|
| 0 | 95.7 | 2.5 | 1.8 | 97.5 |
| 10 | 40.4 | 58.3 | 1.3 | 40.9 |
| 20 | 16.6 | 82.5 | 0.8 | 16.8 |
| 30 | 4.5 | 94.8 | 0.6 | 4.6 |
| 45 | 0.9 | 98.8 | 0.4 | 0.8 |
| 60 | 0 | 99.7 | 0.4 | 0 |

Note: Hb = hemoglobin (B) The procedure of Example 6 (a) was repeated, except the ratio of gas to liquid flow rate was reduced to 2 to 1 using a nitrogen flow rate at 1,000 ml./min. through the gas side of membrane device 16 and a hemoglobin solution flow rate of 500 ml./min. through the other side of membrane oxygenator 16. The results of this procedure are presented in Table II below, showing that the deoxygenation is less effective under these conditions:

TABLE II

| Deoxygenation Time (Min.) % Saturation | % Oxy-hemoglobin | % Deoxy Hb | % Met Hb | % Hb |
|---|---|---|---|---|
| 0 | 95.7 | 3.1 | 1.2 | 96.9 |
| 20 | 43.2 | 55.7 | 1.1 | 43.7 |
| 50 | 27.8 | 70.9 | 1.4 | 28.2 |
| 80 | 21.8 | 76.9 | 1.5 | 22.1 |
| 150 | 14.9 | 83.2 | 1.9 | 15.2 |

(C) The procedure of Example 6 (A) was repeated, except that high purity argon gas (Union Carbide Linde Division) was used. The oxygen was purified to below 1 ppm with the use of oxygen trap 30. All the system parameters were unchanged except that the ratio of argon gas to hemoglobin solution flow rate was 40 to 1, with the argon flow rate of the gas side of membrane device 16 being 4 liters per minute and the hemoglobin solution flow rate through the other side of membrane device 16 being 0.1 liter per minute. The results of this experiment are as shown in Table III below:

TABLE III

| Deoxygenation Time (Min.) % Saturation | % Oxy-hemoglobin | % Deoxy Hb | % Met Hb | % Hb |
| --- | --- | --- | --- | --- |
| 0 | 96.1 | 2.7 | 1.1 | 97.2 |
| 20 | 30.5 | 69.5 | 0 | 30.5 |
| 40 | 18.2 | 82.1 | 0 | 18.1 |
| 70 | 14.1 | 85.9 | 0 | 14.1 |
| 110 | 10.8 | 89.6 | 0 | 10.7 |
| 130 | 9.8 | 90.4 | 0 | 9.8 |

Accordingly, when the above processed solutions of deoxyhemoglobin are heated at a temperature of essentially 45 to 85 degrees C. in accordance with this invention and maintained thereat, one can inactivate substantial amounts of virus present and precipitate substantial amounts of nonhemoglobin proteins. The deoxyhemoglobin present exhibits improved heat stability, reducing losses of hemoglobin during the process.

EXAMPLE 7

Figure 3:
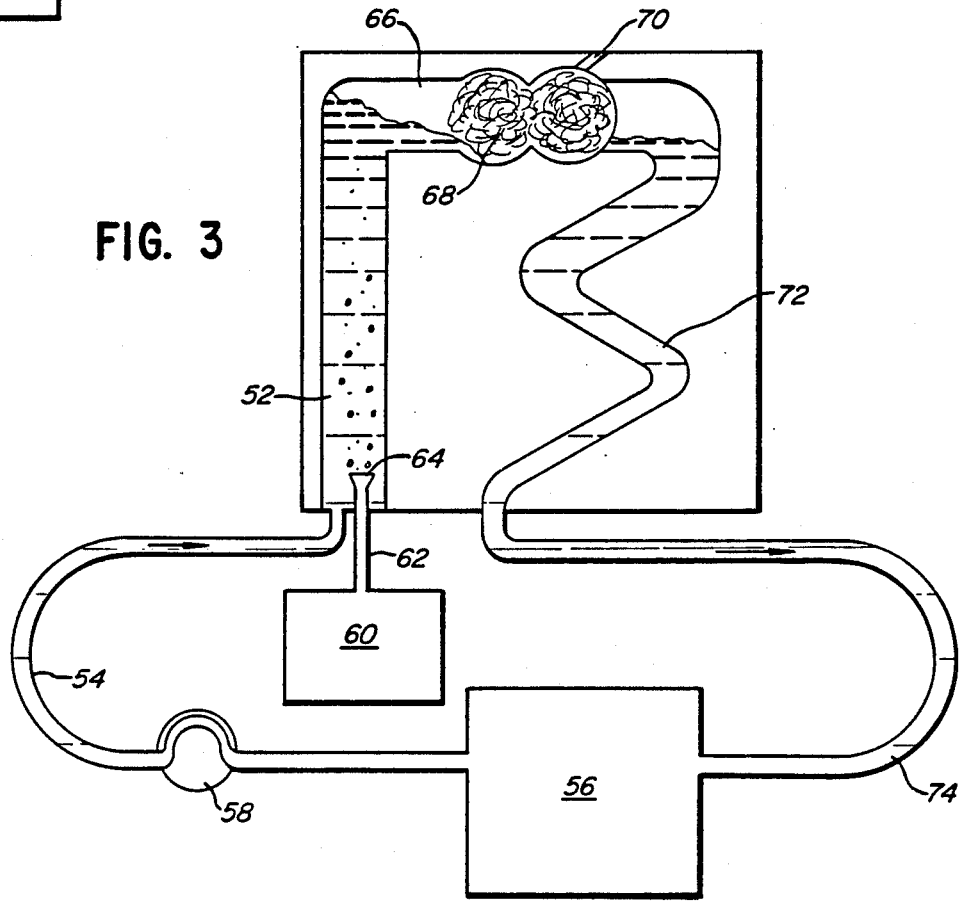
FIG. 3 is an elevational view of apparatus for gas-sparging hemoglobin solutions.

Referring to FIG. 3, apparatus is provided for sparging hemoglobin solutions with oxygen-free inert gas. Basically, known designs of bubble oxygenators for blood may be used for this new purpose, for example designs as disclosed in U.S. Pat. Nos. 3,892,534 or 3,729,377.

Apparatus 50 defines a gas exchange column 52 which has a hemoglobin solution inlet line 54 which leads from solution reservoir 56. Roller pump 58 or the like is provided to circulate the hemoglobin solution from reservoir 56 to column 52 and beyond.

Oxygen-free, inert gas is bubbled into the bottom of column 52 from a gas source 60 through line 62 and porous sparger 64, to cause gas bubbles to rise through the column 52 while filled with hemoglobin solution. At the top of column 52, gas and solution pass through horizontal column 66, containing conventional silicone-coated wire antifoam sponges 68, with the gas being vented through vent 70, and flowing hemoglobin solution passing downwardly through the curved debubbling channel 72. From there, the hemoglobin solution runs through outlet line b74 back to reservoir 56.

By this process, the hemoglobin in solution can be deoxygenated, and thereafter heated as previously described to inactivate virus and to precipitate nonhemoglobin proteins.

EXAMPLE 8

In order to measure the efficacy of hemoglobin solution heat treatment as a viral inactivation procedure, Sindbis, polio, and pseudorabris viruses were seeded into separate solutions of 1 g/dl hemoglobin containing 50 mM sodium dithionite. The solutions were sealed into vials, heated at 60 degrees C., and aliquots removed at various time intervals and stored for subsequent analysis of viral activity. Viral activities were determined by standard plaque assays. The results of this study are shown in Table III below:

TABLE III

| Sample | Virus Titer (Log 10 Plaque Forming Units/ml) | | |
| --- | --- | --- | --- |
| | Sindbis | Polio | Pseudorabies |
| Virus Stock Soln. | 7.45 | 7.50 | 6.09 |
| Unheated Hb Control Soln. | 5.42 | 6.19 | 4.98 |
| Hb Soln. heated 60 C., 30 minutes | 0.00 | 0.00 | 0.00 |
| Hb Soln. heated 60 C., 60 min | 0.00 | 0.00 | 0.00 |
| Hb Soln. heated 60 C., 90 min | 0.00 | 0.00 | 0.00 |
| Hb Soln. heated 60 C., 120 min | 0.00 | 0.00 | 0.00 |

These results demonstrate that all three viruses were rapidly inactivated in the hemoglobin solution under these conditions.

EXAMPLE 9

In this example, stroma-free oxyhemoglobin solution is treated physically as in Example 6, rather than chemically, to remove oxygen from the solution prior to heating.

To effect deoxygenation, two liters of a 0.54 g/dl hemoglobin solution was calculated in a closed system through a SciMed Life System 0.8 square meter membrane oxygenator which was concurrently flushed with nitrogen. After 70 minutes of circulation, the hemoglobin was 96% deoxygenated as assessed spectrophotometrically. The solution was then heated at 60 degrees C. for 5 hours, with a 93% recovery of total hemoglobin content. These results demonstrate that hemoglobin solutions may be successfully heat treated after deoxygenation by passage through a membrane device.

EXAMPLE 10

Approximately 45 ml of solution containing 1 g/dl hemoglobin was sparged as in Example 7 with oxygen-free argon and then heated at 60 degrees C. Absorption spectra were recorded from this solution using a flow through cell before, during and after heating and the relative concentration of oxy, deoxy, and methemoglobin calculated. In this experiment the degree of deoxygenation after sparging was approximately 95%, with further deoxygenation occurring during heating, as shown in Table IV.

TABLE IV

| Sample | Temperature | % oxy Hb | % deoxy Hb | % met Hb |
| --- | --- | --- | --- | --- |
| Hb Soln.-Air Equilibrated | 25 C. | 90 | 9 | 1 |
| Hb Soln.-Argon Sparged | 25 C. | 6 | 95 | 0 |
| Hb Soln.-Heated for 80 minutes | 60 C. | 4 | 96 | 0 |
| Hb Soln.-Heated for 140 minutes | 60 C. | 2 | 98 | 0 |

The hemoglobin formation during heating was minimal and a precipitate of nonhemoglobin proteins observed. The total hemoglobin concentrations were not measurably diminished during the heating period. These data demonstrate that hemoglobin heat treatment may be performed after solution deoxygenation by sparging with inert gas.

EXAMPLE 11

Stroma free hemoglobin was cross-linked by reacting with bis(3,5 dibromosalicyl) fumarate (DBBF), and the resulting product purified by column chromatography. The cross-linked hemoglobin was diafiltered against isotonic sodium phosphate buffer solution, pH 7.4, the concentration adjusted to one g/dL, and aliqots sealed into glass vials. A portion of this solution was admixed with sufficient sodium dithionite to give a final concentration of 50 mM, the pH of the solution adjusted to 7.5 with sodium hydroxide, and aliquots of this solution sealed into glass vials. Aliquots of the hemoglobin mixed with dithionite were heated at 60 degrees C. for 10 hours and the hemoglobin compared to unheated samples after the removal of dithionite by dialysis. The absorption spectra of both heated and unheated samples were virtually identical, as were the oxygen binding characteristics as determined by means of an Aminco Hem-O-Scan Analyzer. These data demonstrate that crosslinked hemoglobin may be heated at 60 degrees C. for 10 hours to inactivate viruses and precipitate contaminating proteins without a significant loss of hemoglobin function.

That which is claimed is:

1. The method of precipitating nonhemoglobin proteins from a hemoglobin solution without substantially precipitating or deactivating said hemoglobin which comprises heating substantially cell-free hemoglobin solution at a temperature of 45 degrees to 85 degrees C., while maintaining said hemoglobin in substantially its deoxyhemoglobin form, whereby heat precipitate nonhemoglobin proteins present are precipitated.

2. The method of claim 1 in which said temperature is 60 degrees to 75 degrees C.

3. The method of claim 2 in which said hemoglobin is maintained in substantially its deoxyhemoglobin form by the presence of a chemical reducing agent under conditions such as the nonhemoglobin protein selectively precipitates but the hemoglobin is not substantially biologically inactivated.

4. The method of claim 3 in which said reducing agent has a reducing potential which is greater than ascorbate.

5. The method of claim 1 in which said reducing agent is a reduced dye, sulfoxy, or sulfhydryl compound.

6. the method of claim 5 wherein the agent is dithionite, bisulphite, metabisulphite, sulphite, reduced glutathione or dithiothreitol.

7. The method of claim 1 in which said time of heating is about 1–15 hours.

* * * * *